(12) United States Patent
Van Balken et al.

(10) Patent No.: US 6,183,780 B1
(45) Date of Patent: *Feb. 6, 2001

(54) ORAL DELAYED IMMEDIATE RELEASE FORMULATION AND METHOD FOR PREPARING THE SAME

(75) Inventors: Paulus M. Van Balken; Jules A. C. Elbers; Henderik W. Frijlink; Wienman E. Philips, all of Weesp (NL)

(73) Assignee: Duphar International Research B.V., Weesp (NL)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/934,196

(22) Filed: Sep. 19, 1997

(30) Foreign Application Priority Data

Sep. 23, 1996 (EP) .................................................. 96202651

(51) Int. Cl.[7] ...................................................... A61K 9/36
(52) U.S. Cl. ...................... 424/480; 424/451; 424/457; 424/463; 424/464; 424/468; 424/474; 424/475
(58) Field of Search .................................... 424/451, 457, 424/463, 464, 468, 474, 475, 480

(56) References Cited

U.S. PATENT DOCUMENTS

| | | | |
|---|---|---|---|
| 4,798,724 | 1/1989 | Khanna | 424/480 |
| 4,897,270 | * 1/1990 | Deutsch et al. | 424/465 |
| 5,229,131 | 7/1993 | Amidon et al. | 424/451 |
| 5,286,497 | 2/1994 | Hendrickson et al. | 424/490 |

FOREIGN PATENT DOCUMENTS

| | | |
|---|---|---|
| 0420459 | * 9/1990 | (EP) . |
| 0396425A | 11/1990 | (EP) . |
| 0431877A | 6/1991 | (EP) . |
| 0502642A | 9/1992 | (EP) . |
| 0655240A | 5/1995 | (EP) . |
| 9319741 | 10/1993 | (WO) . |

* cited by examiner

Primary Examiner—José G. Dees
Assistant Examiner—Kathryne E. Shelborne
(74) Attorney, Agent, or Firm—Stevens, Davis, Miller & Mosher, L.L.P.

(57) ABSTRACT

The invention relates to an Oral Delayed Immediate Release formulation comprising a compressed core containing one or more active substances surrounded with a coating, wherein release of active substance from the core is caused by rupture of the coating after a definite lag-time, said core comprising one or more immediate release carriers and having no substantial swelling properties upon exposure to gastrointestinal fluids. The invention further relates to formulations containing an Immediate Release formulation combined with one or more Oral Delayed Immediate Release formulations with different lag-times and to a method of preparing an Oral Delayed Immediate Release formulation.

The Oral Delayed Immediate Release formulation may be used for the application of active substances whenever a certain lag-time before release is advantageous, such as in be the case of anti-asthmatics, anti-emetics, cardiotonics, vasodilators, anti-vertigo and anti-meniere compounds, anti-hypertensives, sedatives, anti-depressants, anti-anxiety compounds, cortico-steroids, general anti-inflammatory compounds, anti-inflammatory compounds for gastrointestinal use, anti-ulceratives, analgetics, anti-aritmics, anti-rheumatics, anti-arthritic compounds and anti-angina compounds.

The Oral Delayed Immediate Release formulation may also be used for the application of biological active compounds such as proteins, peptides, enzymes, vaccines and oligonucleotides.

28 Claims, 10 Drawing Sheets

US 6,183,780 B1

ORAL DELAYED IMMEDIATE RELEASE FORMULATION AND METHOD FOR PREPARING THE SAME

FIELD OF THE INVENTION

The invention relates to an oral delayed immediate release formulation, to a method for preparing such a formulation and to the combination of a delayed immediate release formulation with an immediate release formulation.

DESCRIPTION OF THE RELATED ART

In general, the aim of medicinal treatment is to deliver an amount of an active substance to the target site within the body, to maintain the necessary therapeutic concentration of the active substance at the target site for some period of time and to avoid the presence or accumulation of the active substance at the non-target site. The concentration of the active substance at the target site as a function of time may be of minor importance as long as the therapeutic concentration is reached and not the toxic level. In this case a simple formulation can be used for administration of the active substance. Sometimes a relatively constant concentration of the active substance may be desired, in which case the active substance may be administered in the form of an appropriate slow release formulation. In a number of situations, however, it is believed that beneficial therapeutic effects can be achieved when the active substance is administered in such a manner that the administration is matched to variations in the body in the course of the 24: hours day. This goal can simply be achieved by administering a normal immediate release formulation just before the point in time that a high concentration of active substance is desired, leading to an immediate pulsatile release of the active substance. In some cases, however, e.g. when said point in time is during the night or early in the morning, the administration can only be performed with severe burden to the patient. In that case, but also in all other cases where improvement of patient compliance is desirable, the active substance can be administered via a formulation that releases the active substance after a certain predetermined lag-time, if desired combined with an immediate release formulation.

Several approaches are known to the preparation of formulations that release active substance after a certain pre-determined lag-time. EP 0210540 describes the so called Time-Controlled Explosion System, a system principally consisting of a swellable core and an outer membrane of water-insoluble material. In this system the release mechanism is based on the fact that gastro-intestinal fluids penetrate through the coating and cause the swelling agent to swell. This swelling results in an "explosion" of the coating, which is followed by the release of the drug. It is claimed that the lag-time of the system can be controlled by the coating thickness. The major disadvantage of this system is that it is not suitable for obtaining a pulsatile release in combination with a longer (6 to 14 hours) lag-time. The variation in lag-time is high, due to the high elasticity of the coating and the irreproducible swelling of the mentioned swelling agents. Moreover, it has been observed that the release is not pulsatile, but requires several hours (1 to 3). Only when short lag-times are used, real pulsatile release occurs.

WO 93/19741 also describes a pharmaceutical formulation for time-controlled release of active substance. In this formulation the release mechanism is based on the fact that the core, containing the active substance, is covered with an erodable layer or a combination of erodable layers, at least one of the erodable layers containing, as a major constituent a water-soluble cellulose derivative or a mixture of water-soluble cellulose derivatives. The disadvantage of this formulation is that it is not easy to prevent leakage during the lag-time, especially when longer lag-times are desired. Furthermore it is difficult to obtain a pre-determined lag time, especially longer than 7 hours, in a reliable and reproducible way.

OBJECTS OF THE INVENTION

It is the purpose of the present invention to deliver a formulation that releases the active substance immediately after a certain pre-determined lag-time in a pulsatile manner, without substantial leakage taking place during the lag-time, Furthermore the lag-time should be controlled in a reliable and reproducible way and it should be possible to produce the formulation by relatively simple and inexpensive formulation methods.

SUMMARY OF THE INVENTION

This goal can be achieved by an Oral Delayed Immediate Release formulation comprising a compressed core containing one or more active substances surrounded with a coating, wherein release of active substance from the core is caused by rupture of the coating after a definite lag-time, said core comprising one or more immediate release carriers and having no substantial swelling properties upon exposure to gastrointestinal fluids.

BRIEF DESCRIPTION OF THE DRAWINGS

FIG. 19(A) shows formulation before exposure to gastrointestinal fluids; FIG. 19(B) shows formulation just after rupture of the coating; FIG. 19(C) shows rest of coating left after release of the core containing the active substance.

DETAILED DESCRIPTION OF THE PREFERRED EMBODIMENTS

Figure 1:
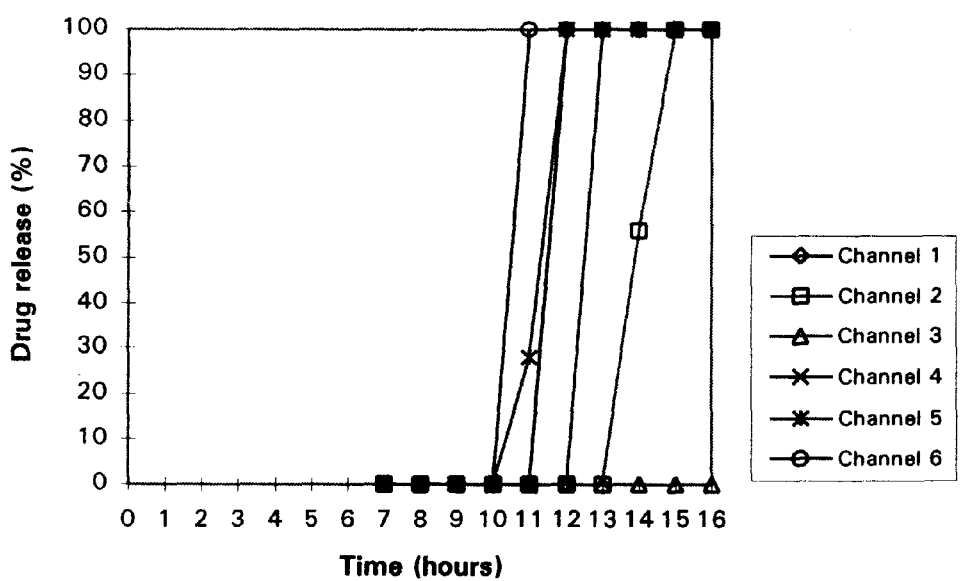
FIG. 1. is a graphic representation of an in-vitro dissolution study of six coated tablets as in Example 2.

In said Oral Delayed Immediate Release formulation the release mechanism is based on the fact that the strength of the coating is gradually decreasing as a result of the impact of the aqueous fluid on the coating material, finally leading to rupture of the coating as a result of the residual stress in the tablet core. Residual stress is always present in a compressed tablet core and is cause by the compression used when the core was formed. The difference with EP 0210540 is that the core of the present invention does not have swelling properties. The lag-time before the release of the active substance in the present invention is caused by the intrinsic properties of the coating material, and not by the intrinsic properties of the core as in EP 0210540. Further the release of active substance is caused by rupture of the coating and not by gradual dissolution or erosion of one of the main components of the coating as in WO 93/19741.

The release time of the active substance after rupture of the coating is dependent on the composition of the core. The carries is composed from the group of common filler-binders, e.g. cellulose, lactose, mannitol, starch and dicalcium phosphate. In order to improve the disintegration of the core after the opening of the coating, preferably a small amount of a compound having swelling properties, such as cross-linked carboxymethylcellulose, is added. The overall composition is chosen in such a way that an immediate release carrier, having no substantial swelling properties is obtained, which means that the composition of the carrier has no influence on the lag-time of the system. An immediate release carrier is defined as a carrier causing a pulsatile release.

The Oral Delayed Immediate Release formulation of the present invention preferably comprises a compressed core containing one or more active substances surrounded with a coating containing one or more polymeric materials, wherein release of active substance(s) from the core is caused by rupture of the coating after a definite lag-time, said core comprising one or more immediate release carriers and having no substantial swelling properties upon exposure to gastrointestinal fluids, and said polymeric coating materials being essentially non-soluble and/or non-erodable in gastrointestinal fluids.

Most preferably the Oral Delayed Immediate Release formulation of the present invention has a coating as defined above, also comprising 2–20% of a water-soluble plasticizing agent and an effective amount of a brittleness-inducing agent.

In this embodiment of the present invention the release mechanism is based on the fact that the water-soluble plasticizer leaks from the coating after the tablet is placed in an aqueous fluid (like the gastro-intestinal fluids). As a result of this process the brittleness of the coating layer increases, and after a certain time the coating will crack as a result of the residual stress in the core of the tablet. The lag time of this system can be influenced in several ways:

When a thicker coating is used the time to dissolve and leak away of the water-soluble plasticizer will increase, as will the time at which the coating cracks.

When more brittleness-inducing material is used, the coating will crack earlier.

When a higher amount of plasticizer is used the lag-time will increase.

Figure 19:
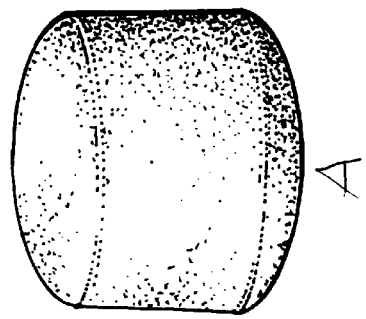
FIG. 19 (A–C) is an electronic scan of a Polaroid photograph which illustrates the behavior of the oral delayed immediate release formulations in gastrointestinal fluids as a function of time.
Figure 19:
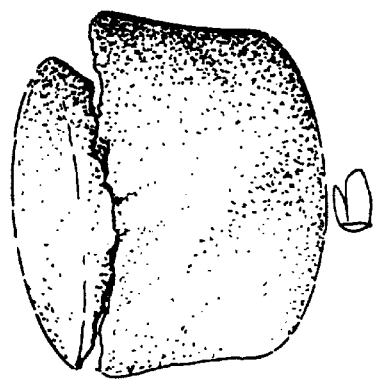
Figure 19:
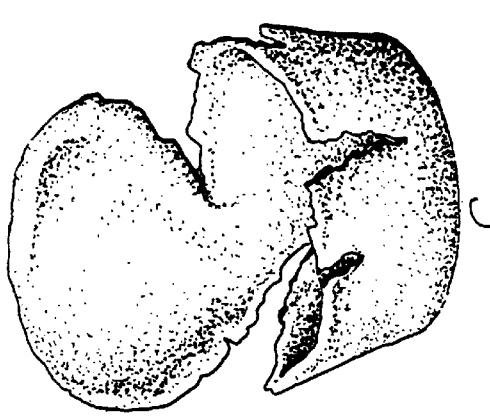

When sharp edges are present on the tablet the cracking will start at the edges resulting in a situation resembling the opening of the cover of a box (see FIG. 19). When the "cover of the box" has been opened, the active substance is immediately released.

In order to obtain a formulation with a reliable lag-time and a real pulsatile release the diameter is preferably more than 2 mm and most preferably more than 5 mm.

The coating material may be selected from the commercial available water-insoluble coating materials such as ethylcellulose, other water-insoluble cellulose derivatives and polymethacrylates. The preferred water-insoluble coating material is ethylcellulose (e.g. Aquacoat®)

As already described above the lag-time before release of the active substance is defined by the elasticity of the coating as a function of time which is determined by the balance between the type and amount of brittleness-inducing agent and the type and amount of plasticizing agent for a certain polymer.

The water-soluble plasticizing agent can be selected from the commercial available plasticizing agents, such as triethyl citrate, tributyl citrate, propylene glycol, polyethylene glycol, triacetin and sodium lauryl sulphate. The amount of water-soluble plasticizing agent that is needed is dependent on the type of compound that is used. For the presently commercially available pharmaceutical plasticizers the effective amount varies between 2 and 20% of the total dry substance of the coating material. The preferred water-soluble plasticizing agent is triethyl citrate (e.g. Citroflex®), in a concentration of between 10% and 20% of the total dry substance of the coating material.

A brittleness-inducing agent is defined as a dose agent which decreases the elasticity of the film which forms the coating. The effective amount of brittleness-inducing agent is dependent on the type of brittleness-inducing agent that is used. The effective amount is 20–40% when talc is used, 3–25% in the case of aerosil and 5–60% in the case of magnesium stearate, all amounts relative to the total dry substance of the coating material. The coating is prepared in such a way that the thickness of the coating remains substantially constant when the formulation is exposed to gastrointestinal fluids. Only the plasticizer leaks away from the coating.

When a coating is used containing smaller amounts of the brittleness-inducing agent, such as the coating described in U.S. Pat No. 5,158,777, no cracking of the coating will occur and the active substance will be released slowly as a result of the permeability of the coating as soon as enough water-soluble plasticizing agent has been leached out.

In order to prevent release of active substance from the formulation by means of diffusion of permeation, the coating should not comprise substantial amounts of polymeric coating materials that are soluble and/or erodable in gastrointestinal fluids. These type of formulations are disclosed in U.S. Pat. No. 4,798,724, describing a formulation containing the water-soluble coating material Klucel®, leading to decomposition of the coating when the formulation is exposed to gastrointestinal fluid, in EP 0431877 describing a coating which is soluble in intestinal juice from pH 5.5 upwards, leading to a pH dependent release of thy active substance instead of a time-dependent release, and in EP 0655 240 describing a formulation wherein the coating is eroded, leading to an increasing permeability and consequently diffusion of the active substance through the coating.

A permeable coating may also obtained when quaternary ammonium groups are present in the polymeric coating material of a specific composition, leading to sustained release of the active compound and not to a pulsatile release after a certain lag-time. Such a sustained release formulation is described in EP 0502642.

The formulation according to the present invention can be used both for human and veterinary applications.

Typical indications wherein an Oral Delayed Immediate Release Formulation will be beneficial are indications wherein a peak level of active substance is desirable in the early morning, such as in the case of antiasthmatics (e.g. bronchodilators), anti-emetics, cardiotonics, vasodilators, anti-vertigo and anti-meniere drugs (e.g. betahistine) and anti-hypertensives. However, also for other indications the formulation can be very useful to improve patient compliance, e.g. for sedatives as diazepam for antidepressants as fluvoxamine and flesinoxan, for anti-anxiety compounds as alprazolam and flesinoxan and for other CNS compounds. Other interesting groups of drugs may be: anti-inflammatory drugs for gastro-intestinal use (for treatment of disorders like Crohn's disease or colitis ulcerosa or irritatable bowel (e.g. mebeverine)), anti-ulceratives, anti-asthmatics, corticosteroids such as prednisone, other anti inflammatory drugs, analgetics, anti-rheumatics, anti-arthritic drugs and anti-angina drugs.

Another class of active compounds that can be formulated in an Oral Delayed Immediate Release formulation are bio-active proteins, peptides, enzymes (e.g. pancreatin), vaccines (e.g. influenza vaccine) and oligonucleotides. Very often these type of compounds are not resistant to the very acidic environment in the stomach. Furthermore it may be desirable to administer said type of compounds in a pulsatile way as recently described by Cardomone et al (J. Contr. Rel. 1997, 47, 205–219) for a delivery system for immunisation against tetanus toxoid.

A further improvement of patient compliance can be reached when formulations with different release lag-times are combined in a single dosage form. Therefore the present invention also relates to an Oral Delayed Immediate Release formulation as defined above, characterized in that said Oral Delayed Immediate Release formulation has a certain release lag-time and is combined in one capsule with an Oral Immediate Release formulation and/or one or more Oral Delayed Immediate Release formulations with a different release lag-time. The capsule may consist of common material, such as gelatin or starch derivatives. In an alternative single dosage form the formulation of the invention is surrounded with an Oral Immediate Release Formulation. Therefore the present invention also relates to an Oral Delayed Immediate Release formulation as defined above, characterized in that said Oral Delayed Immediate Release formulation is surrounded with an Oral Immediate Release formulation.

The present invention also relates to the use of a combination of one or more active substances, core-forming substances and coating-forming substances, for the manufacture of an Oral Delayed Immediate Release formulation comprising a compressed core surrounded with a coating, said core comprising one or more active substances and one or more immediate release carriers, wherein release of active substance is caused by rupture of the outer membrane after a definite lag-time, characterized in that said Oral Delayed Immediate Release formulation has the composition as described above.

The present invention also relates to a method of preparing an Oral Delayed Immediate Release formulation as described above, characterized in that (1) a core is compressed of a mixture comprising one or more active substances and one or more immediate release carriers, (2) the compressed core is coated with a mixture of coating materials, said core and said coating having the properties and/or composition as described above.

As described above the Oral Delayed Immediate Release formulation can be combined with an Oral Immediate Release formulation or an Oral Delayed Immediate Release formulation with a different lag-time in one single embodiment. Therefore the present invention also relates method of preparing an Oral Delayed Immediate Release formulation as described above, characterized in that (1) a core is compressed of a mixture comprising one or more active substances and one or more immediate release carriers, (2) the compressed core is coated with one or more coating materials and that (3) the first Oral Immediate Release formulation is (i) combined in a capsule with an Oral Immediate Release formulation and/or one or more Oral Delayed Immediate Release formulations with a different release lag-time, or (ii) surrounded with an Oral Immediate Release formulation, a mixture of coating materials, said core and said coating having the properties and/or composition as described above.

It is an advantage of the present invention that the formulation can be prepared using commercial available formulation materials and relatively simple and inexpensive formulation methods.

The invention will now be described in greater detail with reference to the following specific Examples.

EXAMPLES

Examples 1

To investigate the influence of the amount of cross-linked carboxymethylcellulose in the core tablets, several coated tablets, with different amount of cross-linked carboxymethylcellulose, are produced. The production of the core tablets is performed in the following way:

1. micro-crystalline cellulose is granulated, by adding the aqueous solution of betahistine.2HCl, in a high shear mixer.
2. the yield of 1. is dried and screened.
3. the yield of 2. is mixed with the talc and optionally with the cross-linked carboxymethylcellulose.
4. the yield of 3. is compressed to tablets of Ø 5.0 mm and a weight of 100 mg each.

The coating of the core tablets is performed in the following way:

5. the coating suspension is prepared by mixing ethylcellulose, plasticizing agent and brittleness-inducing agent in the desired ratio with water, until a suspension with a dry substance content of 20% is obtained.
6. in a coating pan or fluid bed, the yield of 4 (the core tablets), is coated with the yield of 5, until the required weight of the tablets is obtained.

After coating, tablets, having the following composition, in mg per tablet, are obtained:

| Exipients | Exp. a | Exp. b | Exp. c | Exp .d | Exp. e | Exp. f |
|---|---|---|---|---|---|---|
| Core: | | | | | | |
| betahistine · 2HCl | 27.8 | 27.8 | 27.8 | 27.8 | 27.8 | 27.8 |
| micro-crystalline cellulose | 69.2 | 67.2 | 65.2 | 65.2 | 64.2 | 62.2 |
| talc | 3.0 | 3.0 | 3.0 | 3.0 | 3.0 | 3.0 |
| cross-linked carboxymethyl-cellulose | 0.0 | 2.0 | 4.0 | 4.0 | 5.0 | 7.0 |
| Coating: | | | | | | |
| ethylcellulose | 14.3 | 14.1 | 14.5 | 14.1 | 14.3 | 14.5 |
| Citroflex ® 2 | 3.0 | 3.0 | 3.1 | 3.0 | 3.0 | 3.1 |
| talc | 8.6 | 8.5 | 8.7 | 8.5 | 8.6 | 8.7 |
| Total | 125.9 | 125.6 | 126.3 | 125.6 | 125.9 | 126.3 |

In-vitro dissolution studies with the USP apparatus II, with half change release medium and a rotation speed of the paddle of 50 rpm are performed.

The results are summarized in the next table:

| | Core tablets | | |
|---|---|---|---|
| Experiment | Amount cross-linked carboxymethylcellulose (%) | Coating (%) | Mean start time of the release (n = 6) |
| a | 0 | 20.5 | 7.2 hours |
| b | 2 | 20.4 | 6.0 hours |
| c | 4 | 20.8 | 7.0 hours |
| d | 4 | 20.4 | 7.5 hours |
| e | 5 | 20.6 | 7.6 hours |
| f | 7 | 20.8 | 7.5 hours |

From these experiments it can be concluded that the addition of a super disintegrating agent has no influence on the lag-time.

Example 2

Core tablets with the composition of experiment f of example 1 are prepared as described in example 1, followed by coating with a thicker coating.

Composition, in mg per tablet:

| Exipients | Example 2 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 19.6 |
| Citroflex ® 2 | 4.1 |
| talc | 3.9 |
| Total | 127.6 |

In-vitro dissolution study of 6 coated tablets with the USP apparatus II, with water as release medium and a rotation speed of the paddle of 50 rpm gives the following results (also depicted in FIG. 1):

| Example 2 | Release (%) after sampling time (in hours): | | | | | | | | | |
|---|---|---|---|---|---|---|---|---|---|---|
| | 7.0 | 8.0 | 9.0 | 10.0 | 11.0 | 12.0 | 13.0 | 14.0 | 15.0 | 16.0 |
| channel 1 | 0 | 0 | 0 | 0 | 0 | 0 | 100 | 100 | 100 | |
| channel 2 | 0 | 0 | 0 | 0 | 0 | 0 | 0 | 56 | 100 | |
| channel 3 | 0 | 0 | 0 | 0 | 0 | 0 | 0 | 0 | 0 | 0 |
| channel 4 | 0 | 0 | 0 | 0 | 0 | 100 | 100 | 100 | 100 | |
| channel 5 | 0 | 0 | 0 | 0 | 28 | 100 | 100 | 100 | 100 | |
| channel 6 | 0 | 0 | 0 | 0 | 100 | 100 | 100 | 100 | 100 | |

From this experiment it can be concluded that a thicker coating combined with a lower amount of brittleness-inducing agent leads to a longer lag-time.

Example 3

Core tablets with the composition of experiment f of example 1 are prepared as described in example 1, followed by coating with a suspension containing a lower amount of talc.

Composition, in mg per tablet:

| Exipients | Example 3 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 17.6 |
| Citroflex ® 2 | 3.7 |
| talc | 5.3 |
| Total | 126.6 |

Figure 2:
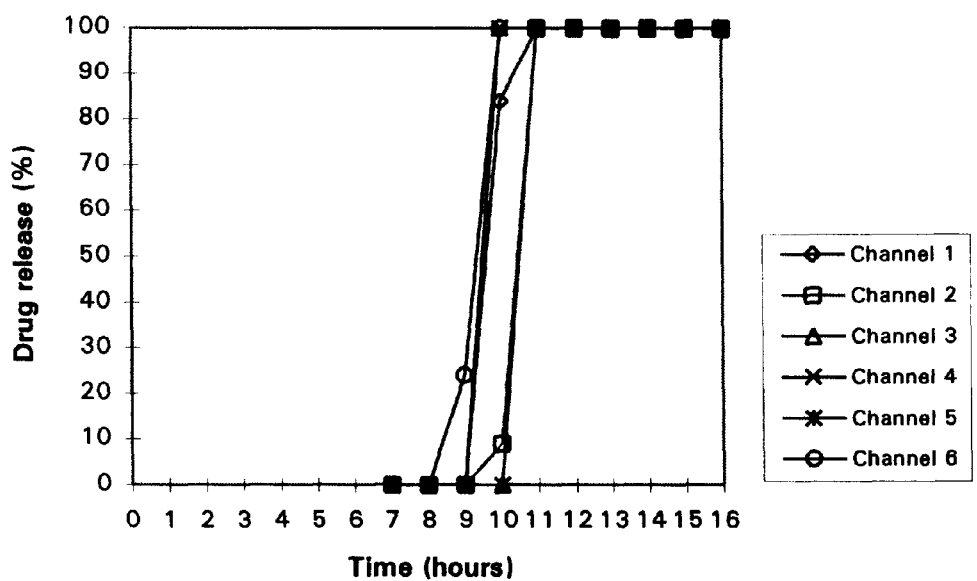
FIG. 2 is a graphic representation of an in-vitro dissolution study of six coated tablets as in Example 3.

In-vitro dissolution study of 6 coated tablets with the USP apparatus II, with water as release medium and a rotation speed of the paddle of 50 rpm gives the following results (also depicted in FIG. 2):

| Example 3 | Release (%) after sampling time (in hours): | | | | | | | | | |
|---|---|---|---|---|---|---|---|---|---|---|
| | 7.0 | 8.0 | 9.0 | 10.0 | 11.0 | 12.0 | 13.0 | 14.0 | 15.0 | 16.0 |
| channel 1 | 0 | 0 | 0 | 84 | 100 | | | | | |
| channel 2 | 0 | 0 | 0 | 9 | 100 | | | | | |
| channel 3 | 0 | 0 | 0 | 0 | 100 | | | | | |
| channel 4 | 0 | 0 | 0 | 100 | 100 | | | | | |
| channel 5 | 0 | 0 | 0 | 0 | 100 | | | | | |
| channel 6 | 0 | 0 | 24 | 100 | 100 | | | | | |

From this experiment it can be concluded that a lower amount of brittleness-inducing agent leads to a longer lag-time.

Example 4

Core tablets with the composition of experiment f of example 1 are prepared as described in example 1, followed by coating with a suspension containing a higher amount of talc.

Composition, in mg per tablet:

| Exipients | Example 4 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 16.2 |
| Citroflex ® 2 | 3.4 |
| talc | 6.5 |
| Total | 126.1 |

Figure 3:
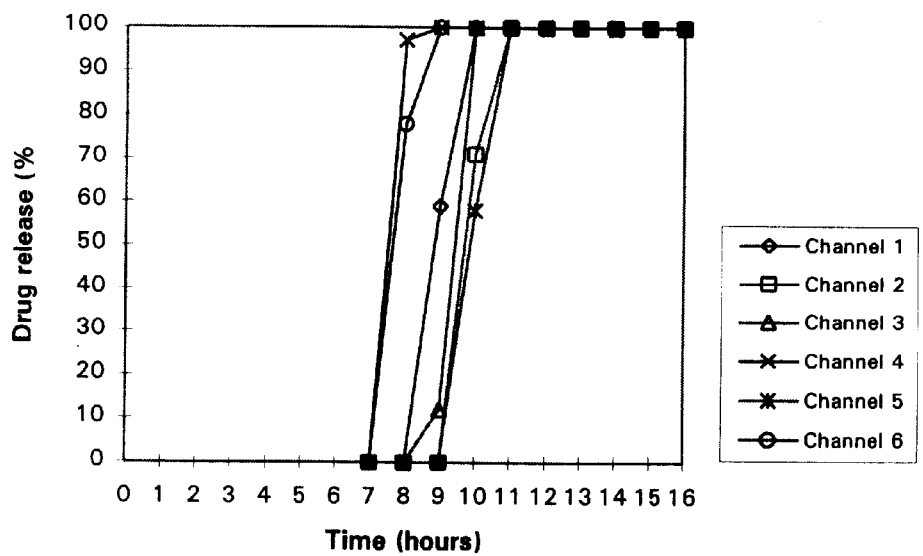
FIG. 3 is a graphic representation of an in-vitro dissolution study of six coated tablets as in Example 4.

In-vitro dissolution study of 6 coated tablets with the USP apparatus II, with water as release medium and a rotation speed of the paddle of 50 rpm gives the following results (also depicted in FIG. 3):

| | Release (%) after sampling time (in hours): | | | | | | | | | |
|---|---|---|---|---|---|---|---|---|---|---|
| Example 4 | 7.0 | 8.0 | 9.0 | 10.0 | 11.0 | 12.0 | 13.0 | 14.0 | 15.0 | 16.0 |
| channel 1 | 0 | 0 | 59 | 100 | 100 | | | | | |
| channel 2 | 0 | 0 | 0 | 71 | 100 | | | | | |
| channel 3 | 0 | 0 | 12 | 100 | 100 | | | | | |
| channel 4 | 0 | 97 | 100 | 100 | 100 | | | | | |
| channel 5 | 0 | 0 | 0 | 58 | 100 | | | | | |
| channel 6 | 0 | 78 | 100 | 100 | 100 | | | | | |

From this experiment and the experiments described in examples 1 and 3 it can be concluded that the lag-time before release can be influenced by the amount of brittleness-inducing agent.

Example 5

Core tablets with the composition of experiment f of example 1 are prepared as described in example 1, followed by coating with a suspension containing a higher amount of talc.

Composition, in mg per tablet:

| Exipients | Example 5 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 15.1 |
| Citroflex ® 2 | 3.2 |
| talc | 7.6 |
| Total | 125.9 |

Figure 4:
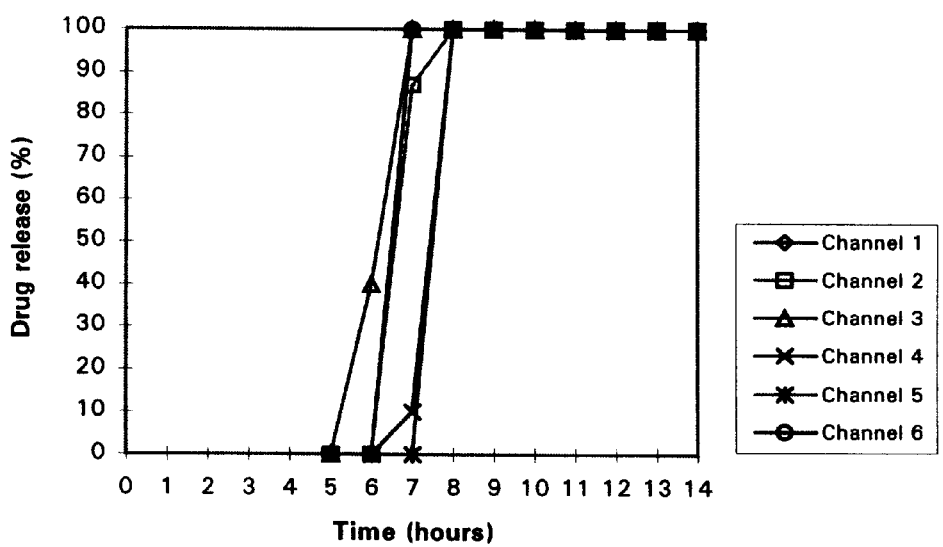
FIG. 4 is a graphic representation of an in-vitro dissolution study of six coated tablets as in Example 5.

In-vitro dissolution study of 6 coated tablets with the USP apparatus II, with water as release medium and a rotation speed of the paddle of 50 rpm gives the following results (also depicted in FIG. 4):

| | Release (%) after sampling time (in hours): | | | | | | | | | | | |
|---|---|---|---|---|---|---|---|---|---|---|---|---|
| Example 5 | 5.0 | 6.0 | 7.0 | 8.0 | 9.0 | 10.0 | 11.0 | 12.0 | 13.0 | 14.0 | 15.0 | 16.0 |
| channel 1 | 0 | 0 | 100 | 100 | 100 | | | | | | | |
| channel 2 | 0 | 0 | 87 | 100 | 100 | | | | | | | |
| channel 3 | 0 | 40 | 100 | 100 | 100 | | | | | | | |
| channel 4 | 0 | 0 | 10 | 100 | 100 | | | | | | | |
| channel 5 | 0 | 0 | 0 | 100 | 100 | | | | | | | |
| channel 6 | 0 | 0 | 100 | 100 | 100 | | | | | | | |

From this experiment and the experiments described in examples 1, 3 and 4 it can be concluded that the lag-time before release can be influenced by the amount of brittleness-inducing agent.

Example 6

Core tablets with the composition of experiment f of example 1 are prepared as described in example 1, followed by coating with a suspension containing a higher amount of talc.

Composition, in mg per tablet:

| Exipients | Example 6 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 15.1 |
| Citroflex ® 2 | 3.2 |
| talc | 7.6 |
| Total | 125.9 |

Figure 5:
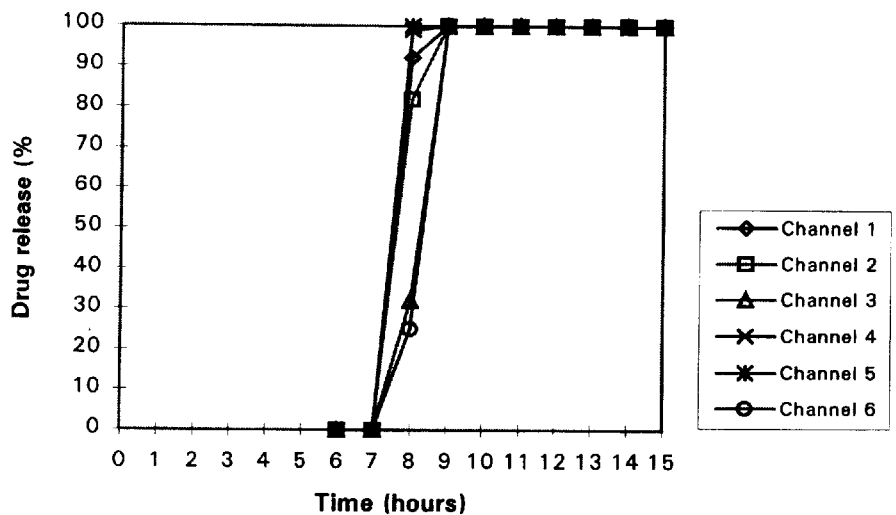
FIG. 5 is a graphic representation of an in-vitro dissolution study of six coated tablets as in Example 6.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 5):

| | Release (%) after sampling time (in hours): | | | | | | | | |
|---|---|---|---|---|---|---|---|---|---|
| Example 6 | 6.0 | 7.0 | 8.0 | 9.0 | 10.0 | 11.0 | 12.0 | 14.0 | 15.0 | 16.0 |
| channel 1 | 0 | 0 | 92 | 100 | 100 | | | | | |
| channel 2 | 0 | 0 | 82 | 100 | 100 | | | | | |
| channel 3 | 0 | 0 | 32 | 100 | 100 | | | | | |
| channel 4 | 0 | 0 | 99 | 100 | 100 | | | | | |
| channel 5 | 0 | 0 | 100 | 100 | 100 | | | | | |
| channel 6 | 0 | 0 | 25 | 100 | 100 | | | | | |

From this experiment and the experiment described in example 5, it can be concluded that the formulation according to the present can be prepared in a reproducible way.

Example 7

Core tablets with the composition of experiment f of example 1 are prepared as described in example 1, followed by coating with a suspension containing magnesium stearate as brittleness-inducing agent instead of talc.

Composition, in mg per tablet:

| Exipients | Example 7 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 13.1 |
| Citroflex ® 2 | 2.8 |
| Mg stearate | 3.9 |
| Total | 119.8 |

Figure 6:
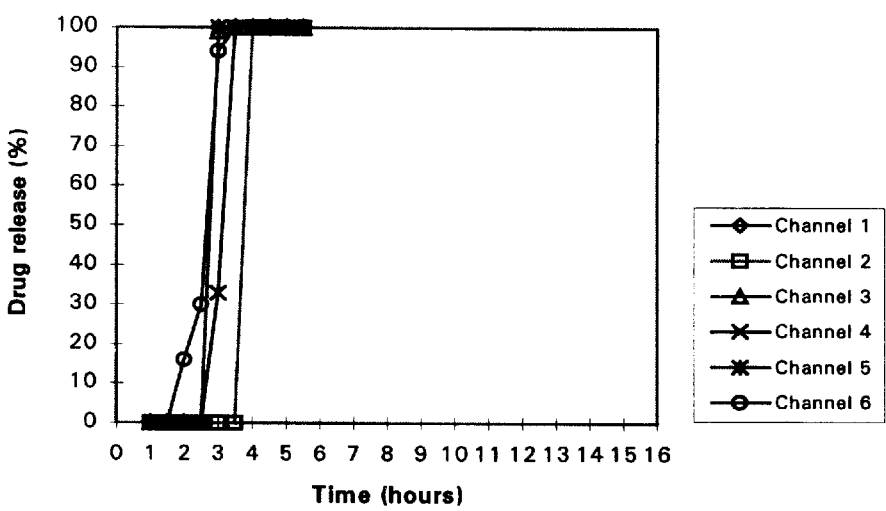
FIG. 6 is a graphic representation of an in-vitro dissolution study of six coated tablets as in Example 7.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 6):

| | Release (%) after sampling time (in hours): | | | | | | | | | |
|---|---|---|---|---|---|---|---|---|---|---|
| Example 7 | 1.0 | 1.5 | 2.0 | 2.5 | 3.0 | 3.5 | 4.0 | 4.5 | 5.0 | 5.5 |
| channel 1 | 0 | 0 | 0 | 0 | 100 | 100 | 100 | | | |
| channel 2 | 0 | 0 | 0 | 0 | 0 | 0 | 100 | | | |
| channel 3 | 0 | 0 | 0 | 0 | 99 | 100 | 100 | | | |
| channel 4 | 0 | 0 | 0 | 0 | 33 | 100 | 100 | | | |
| channel 5 | 0 | 0 | 0 | 0 | 100 | 100 | 100 | | | |
| channel 6 | 0 | 0 | 16 | 30 | 94 | 100 | 100 | | | |

From this experiment it can be concluded that the type of brittleness-inducing agent in the coating has a large influence on the lag-time before release of the drug substance.

Example 8

Core tablets with the composition of experiment f of example 1 are prepared as described in example 1, followed by coating with a suspension containing triacetyl glycerine as plasticizing agent instead of Citroflex®.

Composition, in mg per tablet:

| Exipients | Example 8 |
|---|---|
| Core: | |
| betahistine · 2HCl | 27.8 |
| micro-crystalline cellulose | 62.2 |
| talc | 3.0 |
| cross-linked carboxymethylcellulose | 7.0 |

-continued

| Exipients | Example 8 |
|---|---|
| Coating: | |
| ethylcellulose | 14.1 |
| triacetyl glycerine | 3.0 |
| talc | 8.5 |
| Total | 125.6 |

Figure 7:
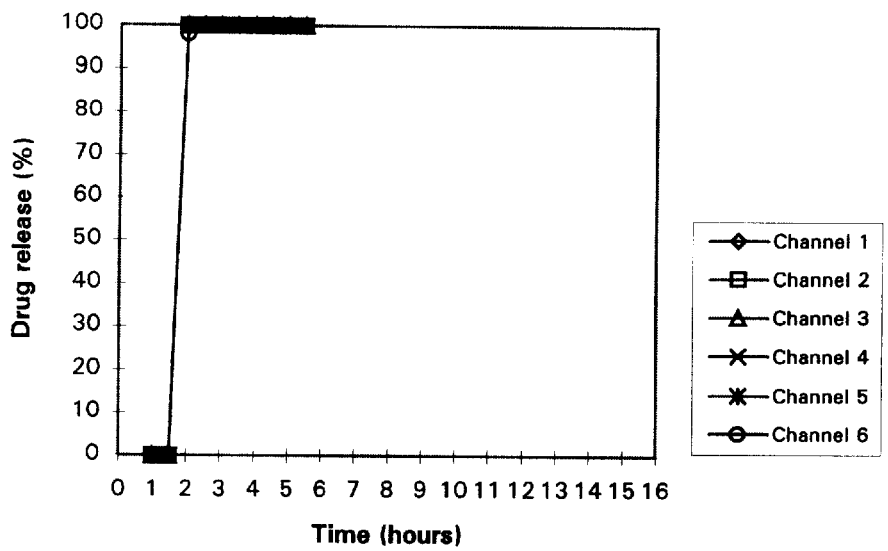
FIG. 7 is a graphic representation of an in-vitro dissolution study of six coated tablets as in Example 8.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 7):

| | Release (%) after sampling time (in hours): | | | | | | | | | |
|---|---|---|---|---|---|---|---|---|---|---|
| Example 8 | 1.0 | 1.5 | 2.0 | 2.5 | 3.0 | 3.5 | 4.0 | 4.5 | 5.0 | 5.5 |
| channel 1 | 6 | 0 | 100 | 100 | | | | | | |
| channel 2 | 0 | 0 | 100 | 100 | | | | | | |
| channel 3 | 0 | 0 | 100 | 100 | | | | | | |
| channel 4 | 0 | 0 | 100 | 100 | | | | | | |
| channel 5 | 0 | 0 | 100 | 100 | | | | | | |
| channel 6 | 0 | 0 | 98 | 100 | | | | | | |

From this experiment and the experiments described in example 1, it can be concluded that type of plasticizing agent in the coating has a large influence on the lag-time before release of the drug substance.

Example 9

Core tablets with the composition of experiment a of example 1 are prepared as described in example 1, followed by coating.

Composition, in mg per tablet:

| Exipients | Example 9 |
|---|---|
| Core: | |
| betahistine · 2HCl | 28.8 |
| micro-crystalline cellulose | 68.3 |
| talc | 2.9 |
| cross-linked carboxymethylcellulose | 0 |
| Coating: | |
| ethylcellulose | 14.1 |

-continued

| Exipients | Example 9 |
|---|---|
| Citroflex ® 2 | 3.0 |
| talc | 8.5 |
| Total | 125.6 |

Figure 8:
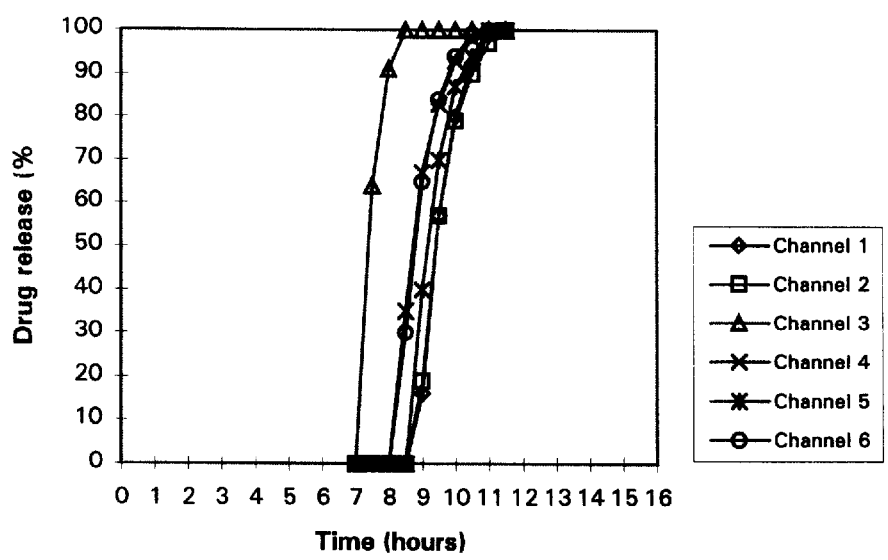
FIG. 8 is a graphic representation of an in-vitro dissolution study of six coated tablets as in Example 9.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 8):

| | Release (%) after sampling time (in hours): | | | | | | | | | | | | |
|---|---|---|---|---|---|---|---|---|---|---|---|---|
| Example 9 | 7.0 | 7.5 | 8.0 | 8.5 | 9.0 | 9.5 | 10.0 | 10.5 | 11.0 | 11.5 | 12.0 | 12.5 | 13.0 |
| channel 1 | 0 | 0 | 0 | 6 | 16 | 57 | 80 | 92 | 99 | 100 | | | |
| channel 2 | 0 | 0 | 0 | 0 | 19 | 57 | 79 | 90 | 97 | 100 | | | |
| channel 3 | 0 | 64 | 91 | 100 | 100 | 100 | 100 | 100 | 100 | 100 | | | |
| channel 4 | 0 | 0 | 0 | 35 | 67 | 83 | 93 | 98 | 100 | 100 | | | |
| channel 5 | 0 | 0 | 0 | 0 | 40 | 70 | 87 | 94 | 100 | 100 | | | |
| channel 6 | 0 | 0 | 0 | 30 | 65 | 84 | 94 | 99 | 100 | 100 | | | |

From this experiment it can be concluded that the absence of a small amount of a compound having swelling properties leads to a more gradual release of the drug substance after the lag-time.

Example 10

Core tablets with about the composition of experiment d of example 1 are prepared as described in example 1, followed by coating as described in example 1.

Composition, in mg per tablet:

| Exipients | Example 10 |
|---|---|
| Core: | |
| betahistine · 2HCl | 27.8 |
| micro-crystalline cellulose | 65.7 |
| talc | 2.8 |
| cross-linked carboxymethylcellulose | 3.7 |
| Coating: | |
| ethylcellulose | 14.2 |
| Citroflex ® 2 | 3.0 |
| talc | 8.6 |
| Total | 125.9 |

Figure 9:
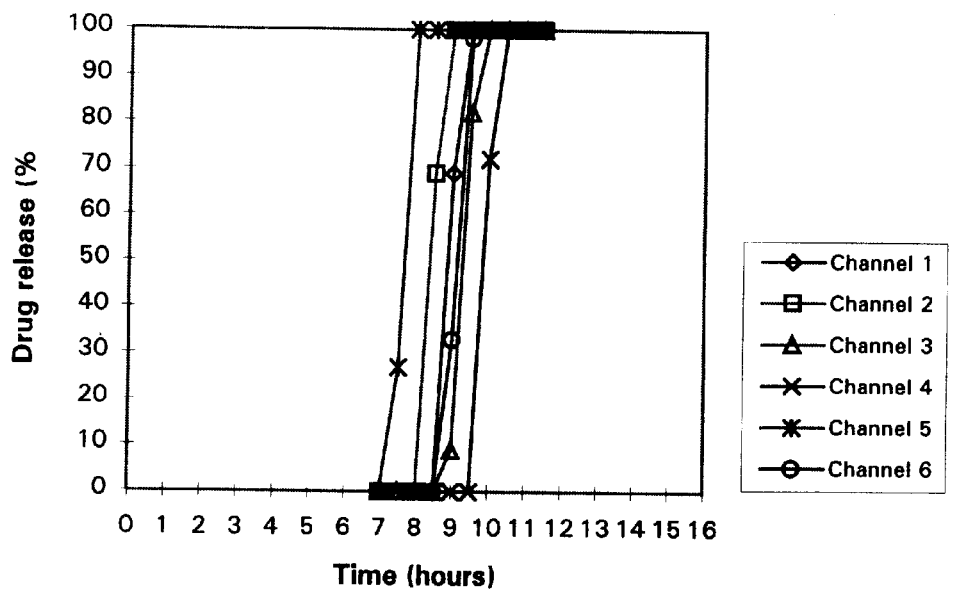
FIG. 9 is a graphic representation of an in-vitro dissolution study of six coated tablets as in Example 10.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 9):

| | Release (%) after sampling time (in hours): | | | | | | | | | | | | |
|---|---|---|---|---|---|---|---|---|---|---|---|---|---|
| Example 10 | 7.0 | 7.5 | 8.0 | 8.5 | 9.0 | 9.5 | 10.0 | 10.5 | 11.0 | 11.5 | 12.0 | 12.5 | 13.0 |
| channel 1 | 0 | 0 | 0 | 0 | 69 | 100 | 100 | 100 | | | | | |
| channel 2 | 0 | 0 | 0 | 69 | 100 | 100 | 100 | 100 | | | | | |
| channel 3 | 0 | 0 | 0 | 0 | 9 | 82 | 100 | 100 | | | | | |
| channel 4 | 0 | 0 | 0 | 0 | 0 | 0 | 72 | 100 | | | | | |
| channel 5 | 0 | 27 | 100 | 100 | 100 | 100 | 100 | 100 | | | | | |
| channel 6 | 0 | 0 | 0 | 0 | 33 | 98 | 100 | 100 | | | | | |

Example 11

Core tablets with about the composition of experiment f of example 1 are prepared as described in example 1, followed by coating as described in example 1.

Composition, in mg per tablet:

| Exipients | Example 11 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 14.5 |
| Citroflex ® 2 | 3.0 |
| talc | 8.7 |
| Total | 126.2 |

Figure 10:
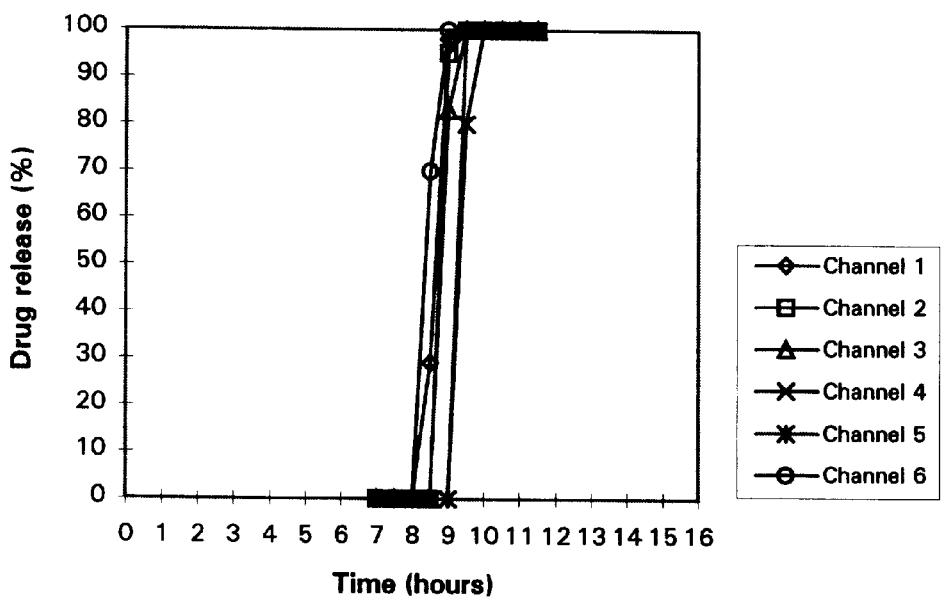
FIG. 10 is a graphic representation of an in-vitro dissolution study of six coated tablets as in Example 11.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 10):

Example 12

Core tablets with the composition of experiment f of example 1 are prepared as described in example 1, followed by coating with a higher amount of coating with the same composition as in experiment f of example 1.

Composition, in mg per tablet:

| Exipients | Example 12 |
|---|---|
| Core: | |
| betahistine · 2HCl | 27.8 |
| micro-crystalline cellulose | 62.2 |
| talc | 3.0 |
| cross-linked carboxymethylcellulose | 7.0 |
| Coating: | |
| ethylcellulose | 21.2 |
| Citroflex ® 2 | 4.5 |
| talc | 12.7 |
| Total | 138.4 |

Figure 11:
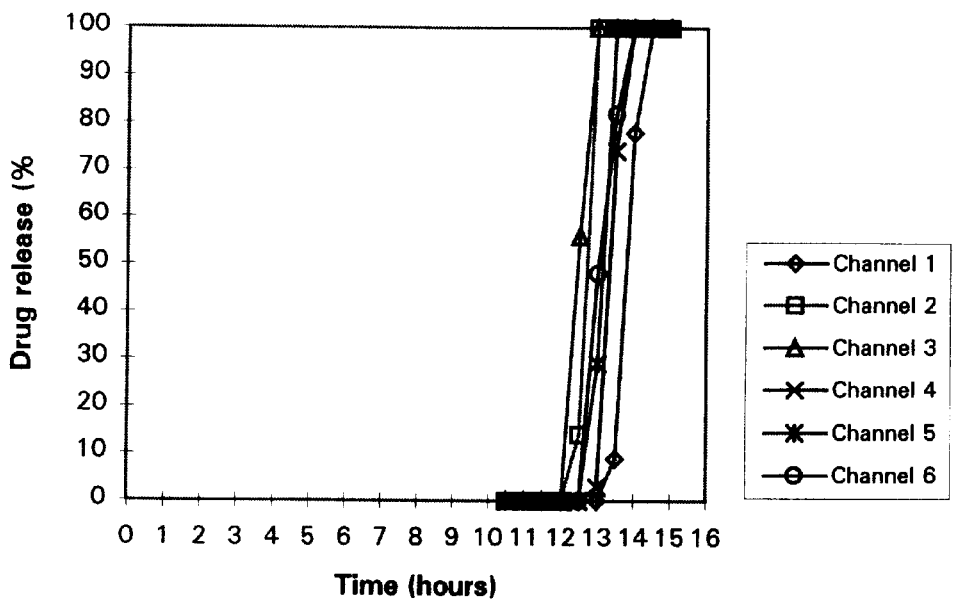
FIG. 11 is a graphic representation of an in-vitro dissolution study of six coated tablets as in Example 12.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 11):

| | Release (%) after sampling time (in hours): | | | | | | | | | | | | |
|---|---|---|---|---|---|---|---|---|---|---|---|---|---|
| Example 11 | 7.0 | 7.5 | 8.0 | 8.5 | 9.0 | 9.5 | 10.0 | 10.5 | 11.0 | 11.5 | 12.0 | 12.5 | 13.0 |
| channel 1 | | | | 0 | 29 | 98 | 100 | 100 | | | | | |
| channel 2 | | | | 0 | 0 | 95 | 100 | 100 | | | | | |
| channel 3 | | | | 0 | 0 | 83 | 100 | 100 | | | | | |
| channel 4 | | | | 0 | 0 | 0 | 80 | 100 | | | | | |
| channel 5 | | | | 0 | 0 | 0 | 100 | 100 | | | | | |
| channel 6 | | | | 0 | 70 | 100 | 100 | 100 | | | | | |

| | Release (%) after sampling time (in hours): | | | | | | | | | | |
|---|---|---|---|---|---|---|---|---|---|---|---|
| Example 12 | 9.0 | 9.5 | 10.0 | 10.5 | 11.0 | 11.5 | 12.0 | 12.5 | 13.0 | 13.5 | 14.0 | 14.5 |
| channel 1 | | | | | | | 0 | 0 | 0 | 9 | 78 | 100 |
| channel 2 | | | | | | | 0 | 14 | 100 | 100 | 100 | 100 |
| channel 3 | | | | | | | 0 | 56 | 100 | 100 | 100 | 100 |
| channel 4 | | | | | | | 0 | 0 | 3 | 74 | 100 | 100 |
| channel 5 | | | | | | | 0 | 0 | 29 | 100 | 100 | 100 |
| channel 6 | | | | | | | 0 | 0 | 48 | 82 | 100 | 100 |

From this experiment it can be concluded that a thicker coating of the same relative composition as in the experiments described in example 1 leads to a longer lag-time.

Example 13

Core tablets with the composition of experiment c of example 1 are prepared as described in example 1, followed by coating a lower amount of coating material as described in experiment c of example 1, on a scale of 100,000 (10 kg) coated tablets.

Composition, in mg per tablet:

| Exipients | Example 13 |
|---|---|
| Core: | |
| betahistine · 2HCl | 27.8 |
| micro-crystalline cellulose | 65.2 |
| talc | 3.0 |
| cross-linked carboxymethylcellulose | 4.0 |
| Coating: | |
| ethylcellulose | 9.0 |
| Citroflex ® 2 | 1.9 |
| talc | 6.8 |
| Total | 117.7 |

Figure 12:
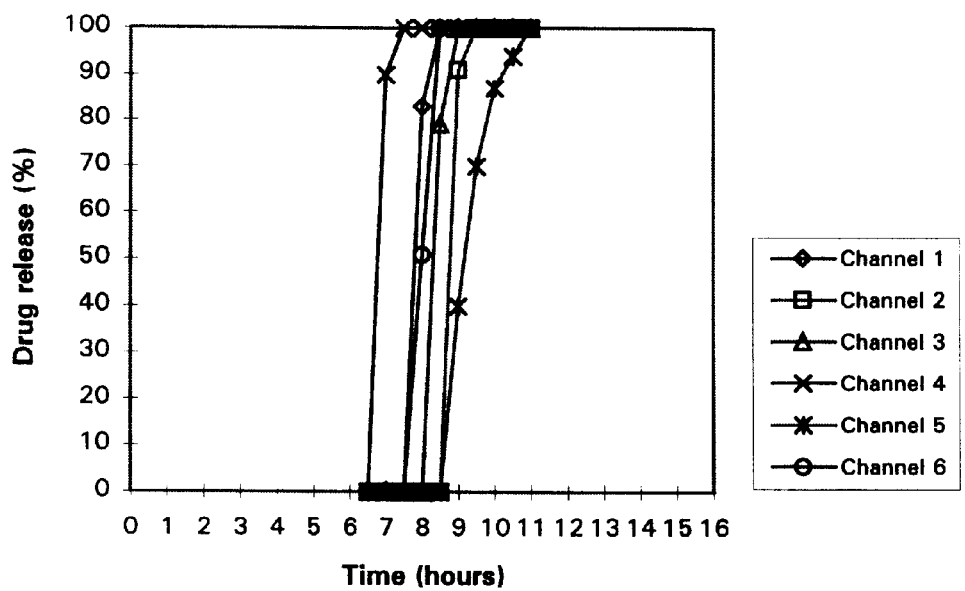
FIG. 12 is a graphic representation of an in-vitro dissolution study of six coated tablets as in Example 13.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 12):

From this experiment it can be concluded that the invented formulation can be prepared on a scale of 100,000 (10 kg) coated tablets.

Example 14

Core tablets with the composition of experiment c of example 1 are prepared as described in example 1, followed by coating a lower amount of coating material as described in experiment c of example 1, on a scale of 500,000 (50 kg) coated tablets. Composition, in mg per tablet:

| Exipients | Example 14 |
|---|---|
| Core: | |
| betahistine · 2HCl | 27.8 |
| micro-crystalline cellulose | 65.2 |
| talc | 3.0 |
| cross-linked carboxymethylcellulose | 4.0 |
| Coating: | |
| ethylcellulose | 10.3 |
| Citroflex ® 2 | 2.2 |
| talc | 7.7 |
| Total | 120.2 |

Figure 13:
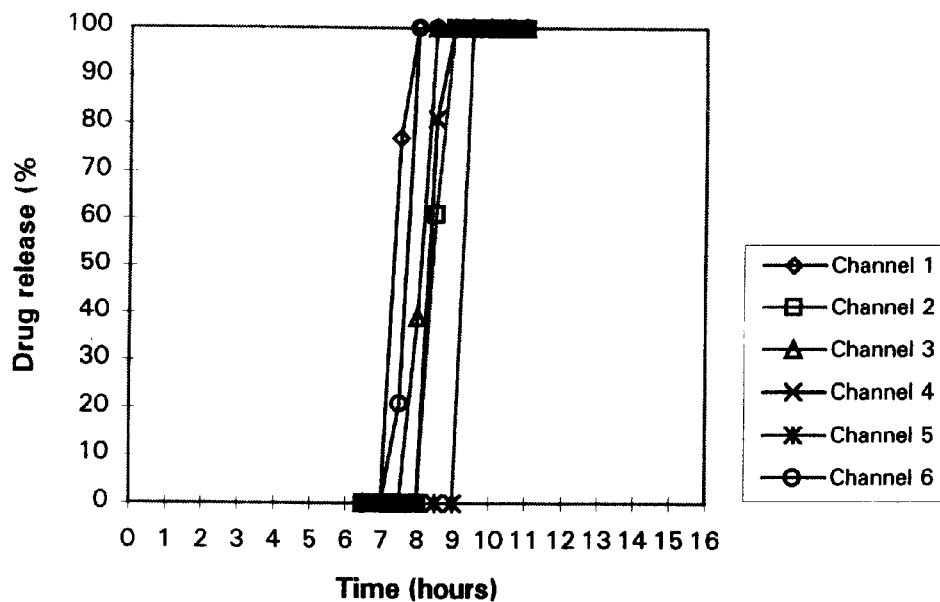
FIG. 13 is a graphic representation of an in-vitro dissolution study of six coated tablets as in Example 14.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 13):

| | Release (%) after sampling time (in hours): | | | | | | | | | | |
|---|---|---|---|---|---|---|---|---|---|---|---|
| Example 13 | 7.0 | 7.5 | 8.0 | 8.5 | 9.0 | 9.5 | 10.0 | 10.5 | 11.0 | 11.5 | 12.0 | 12.5 |
| channel 1 | 0 | 0 | 83 | 100 | 100 | 100 | 100 | 100 | 100 | | | |
| channel 1 | 0 | 0 | 0 | 0 | 91 | 100 | 100 | 100 | 100 | | | |
| channel 3 | 6 | 0 | 0 | 79 | 100 | 100 | 100 | 100 | 100 | | | |
| channel 4 | 90 | 100 | 100 | 100 | 100 | 100 | 100 | 100 | 100 | | | |
| channel 5 | 0 | 0 | 0 | 0 | 40 | 70 | 87 | 94 | 100 | | | |
| channel 6 | 0 | 0 | 51 | 100 | 100 | 100 | 100 | 100 | 100 | | | |

| Example 14 | Release (%) after sampling time (in hours): | | | | | | | | | | |
|---|---|---|---|---|---|---|---|---|---|---|---|
| | 7.0 | 7.5 | 8.0 | 8.5 | 9.0 | 9.5 | 10.0 | 10.5 | 11.0 | 11.5 | 12.0 |
| channel 1 | 0 | 77 | 100 | 100 | 100 | 100 | | | | | |
| channel 2 | 0 | 0 | 0 | 61 | 100 | 100 | | | | | |
| channel 3 | 0 | 0 | 39 | 100 | 100 | 100 | | | | | |
| channel 4 | 0 | 0 | 0 | 81 | 100 | 100 | | | | | |
| channel 5 | 0 | 0 | 0 | 0 | 0 | 100 | | | | | |
| channel 6 | 0 | 21 | 100 | 100 | 100 | 100 | | | | | |

From this experiment it can be concluded that the invented formulation can be prepared on a scale of 500,000 (50 kg) coated tablets.

Example 15

In an exploratory, three-way cross-over bioavailability study the rate and the extent of absorption of betahistine after oral administration of conventional and experimental oral delayed immediate release (TSR) betahistine formulations was investigated. In addition, the safety and tolerability of these betahistine formulations was evaluated. A TSR formulation consisted of a gelatin capsule containing an immediate release formulation and a delayed immediate release formulation as described in example 11 (TSR(0/8)) or example 12 (TSR(0/12)). Eight healthy male subjects between 18–45 years and with a weight between 60–95 kg were included. The eligibility screening consisted of a clinical laboratory examination, medical history, vital signs, ECG and tests on drugs of abuse.

There were four treatments relevant for this application: I: conventional 24 mg formulation at t=0 h and t=8 h; II: conventional 24 mg formulation at t=0 h and t=12 h.; III: TSR (0/8) C 48 mg formulation at t=0 and IV: TSR (0/12) D 48 mg formulation at t=0. Four subjects received treatments I and III and four subjects received treatments II and IV.

The washout period between treatments (morning doses) was 48 hours. The total study duration was 8 days. Urine sampling was done before each dose and in 2 hours fractions up to 18 h, 18–24 h, 24–36 h and 36–48 h after each dose. Safety assessments were done once on screening and after study termination.

Figure 14:
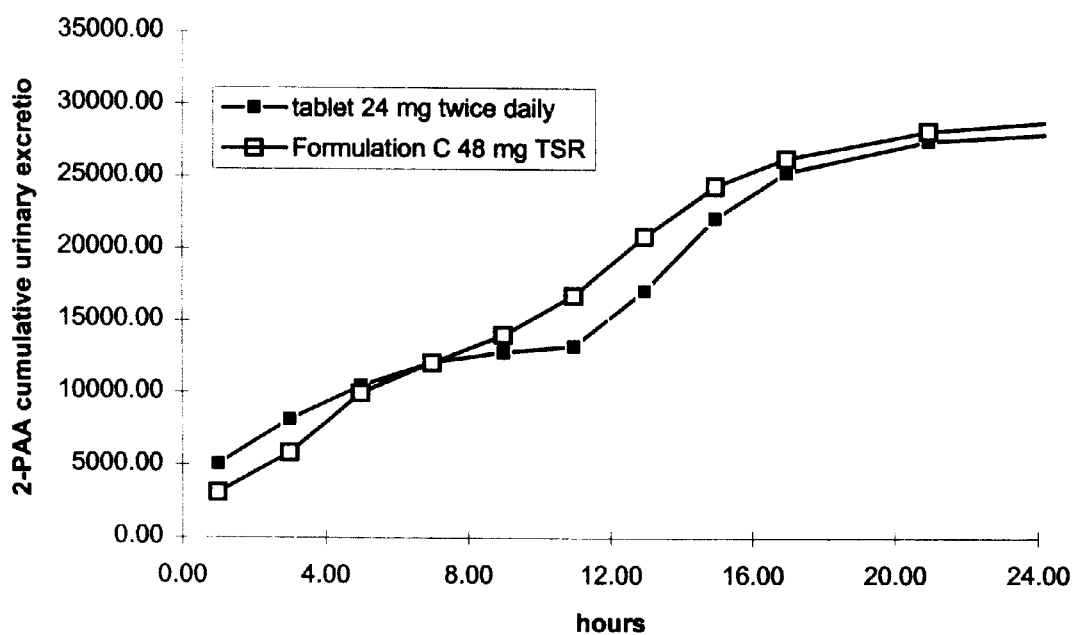
FIG. 14 is a graphic representation of an in-vitro dissolution study of six coated tablets as in Example 15.

The urine samples were analyzed for the concentration of 2-PAA, the major metabolite of betahistine. The cumulative urinary excretion of 2-PAA in the urine was calculated for each treatment. The results showed that formulation C (treatment III) released one dose just after intake and the second dose 12 hours after the first dose. FIG. 14 shows that the urinary excretion profile after treatment III is comparable with that after treatment II, in which conventional tablets were taken twice daily. The safety and tolerability data showed that all treatments were well tolerated. All subjects completed the trial. No clinical significant abnormalities in safety parameters occurred.

Example 16

To investigate the applicability of the present invention in the formulation of prednisone, core tablets containing prednisone are prepared by the procedure described in example 1, followed by coating according to the procedure described in example 1.

Composition, in mg per tablet:

| Excipients | Example 16 |
|---|---|
| Core: | |
| prednisone | 4.2 |
| micro-crystalline cellulose | 132.4 |
| talc | 4.1 |
| cross-linked carboxymethylcellulose | 5.4 |
| Coating: | |
| ethylcellulose | 23.4 |
| Citroflex ® 2 | 4.9 |
| talc | 14.1 |
| Total | 188.5 |

Figure 15:
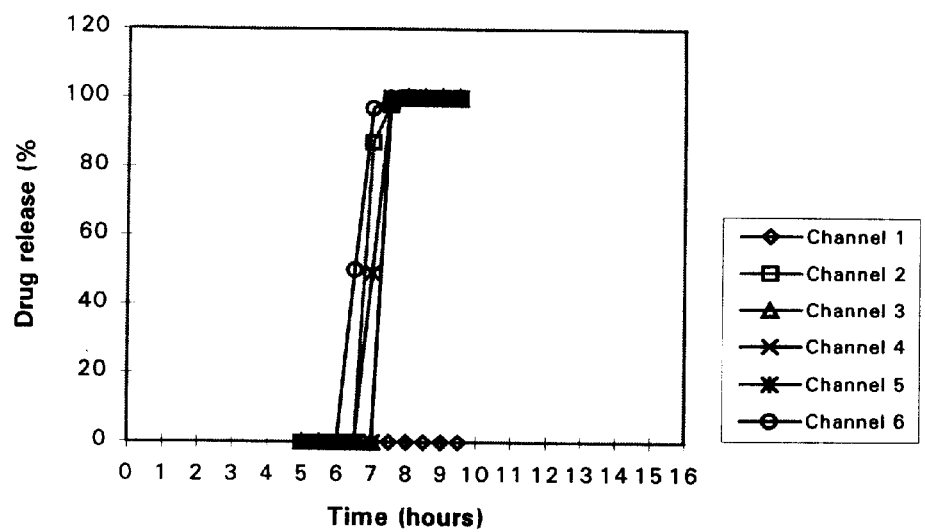
FIG. 15 is a graphic representation of an in-vitro dissolution study of coated tablets as in Example 16.

In-vitro dissolution study of coated tablets with the USP apparatus II, with water as release medium and a rotation speed of the paddle of 50 rpm gives the following results (also depicted in FIG. 15):

| Prednison Example 16 | Release (%) after sampling time (in hours): | | | | | | | | | | | | |
|---|---|---|---|---|---|---|---|---|---|---|---|---|---|
| | 5 | 5.5 | 6 | 6.5 | 7 | 7.5 | 8 | 8.5 | 9 | 9.5 | 10 | 10.5 | 11 |
| Channel 1 | 0 | 0 | 0 | 0 | 0 | 0 | 0 | 0 | 0 | 0 | 0 | 0 | 0 |
| Channel 2 | 0 | 0 | 0 | 0 | 87 | 98 | 100 | 100 | 100 | 100 | 100 | 100 | 100 |
| Channel 3 | 0 | 0 | 0 | 0 | 0 | 99 | 100 | 100 | 100 | 100 | 100 | 100 | 100 |
| Channel 4 | 0 | 0 | 0 | 0 | 0 | 100 | 100 | 100 | 100 | 100 | 100 | 100 | 100 |
| Channel 5 | 0 | 0 | 0 | 0 | 49 | 100 | 100 | 100 | 100 | 100 | 100 | 100 | 100 |
| Channel 6 | 0 | 0 | 0 | 50 | 97 | 100 | 100 | 100 | 100 | 100 | 100 | 100 | 100 |

From the experiments it can be concluded that it is possible to prepare an Oral Immediate Release formulation of prednisone, according to the present invention.

Example 17

To investigate the applicability of the present invention in the formulation of flesinoxan, core tablets containing flesinoxan are prepared by the procedure described in example 1, followed by coating according to the procedure described in example 1.

Composition, in mg per tablet:

| Excipients | Example 17 |
|---|---|
| Core: | |
| flesinoxan | 19.9 |
| microcrystalline cellulose | 70.4 |
| talc | 4.5 |
| cross-linked carboxymethylcellulose | 3.5 |
| Coating: | |
| ethylcellulose | 20.2 |
| Citroflex ® 2 | 4.2 |
| talc | 12.1 |
| Total | 134.8 |

Figure 16:
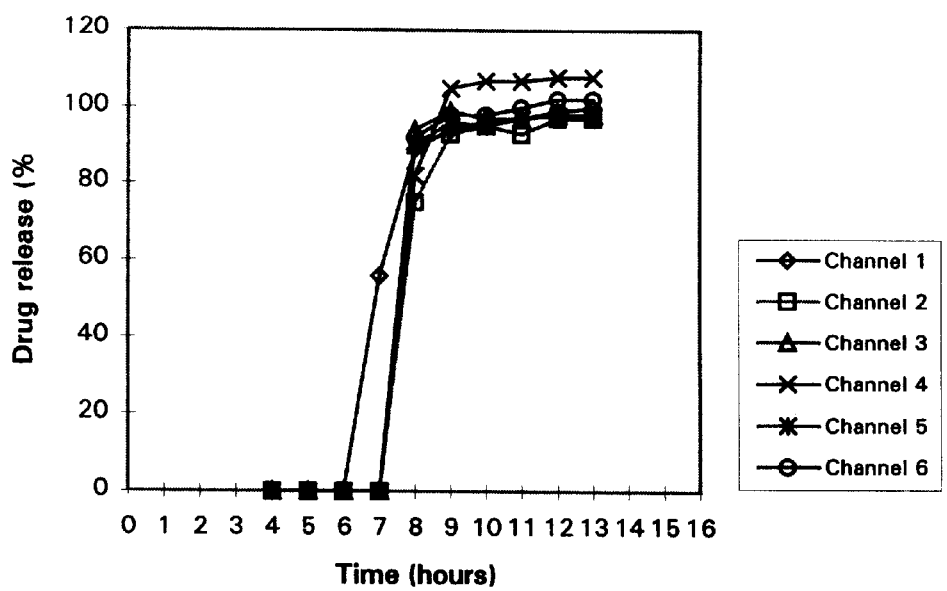
FIG. 16 is a graphic representation of an in-vitro dissolution study of six coated tablets as in Example 17.

In-vitro dissolution study of 6 coated tablets with the USP apparatus II, with water as release medium and a rotation speed of the paddle of 50 rpm gives the following results (also depicted in FIG. 16):

| Flesinoxan | Release (%) after sampling time (in hours): | | | | | | | | | | | | |
|---|---|---|---|---|---|---|---|---|---|---|---|---|---|
| Example 17 | 1 | 2 | 3 | 4 | 5 | 6 | 7 | 8 | 9 | 10 | 11 | 12 | 13 |
| Channel 1 | 0 | 0 | 0 | 0 | 0 | 0 | 56 | 89 | 94 | 96 | 97 | 99 | 100 |
| Channel 2 | 0 | 0 | 0 | 0 | 0 | 0 | 0 | 75 | 93 | 95 | 93 | 97 | 97 |
| Channel 3 | 0 | 0 | 0 | 0 | 0 | 0 | 0 | 94 | 99 | 97 | 97 | 98 | 98 |
| Channel 4 | 0 | 0 | 0 | 0 | 0 | 0 | 0 | 82 | 105 | 107 | 107 | 108 | 108 |
| Channel 5 | 0 | 0 | 0 | 0 | 0 | 0 | 0 | 90 | 96 | 95 | 97 | 98 | 98 |
| Channel 6 | 0 | 0 | 0 | 0 | 0 | 0 | 0 | 92 | 98 | 98 | 100 | 102 | 102 |

From the experiments it can be concluded that it is possible to prepare an Oral Immediate Release formulation of flesinoxan, according to the present invention.

Example 18

To investigate the applicability of the present invention in the formulation of diazepam, core tablets containing diazepam are prepared by the procedure described in example 1, followed by coating according to the procedure described in example 1.

Composition, in mg per tablet:

| Excipients | Example 18 |
|---|---|
| Core: | |
| diazepam | 3.6 |
| micro-crystalline cellulose | 103.0 |
| talc | 3.5 |
| cross-linked carboxymethylcellulose | 4.7 |
| Coating: | |
| ethylcellulose | 14.8 |
| Citroflex ® 2 | 3.1 |
| talc | 8.9 |
| Total | 141.6 |

Figure 17:
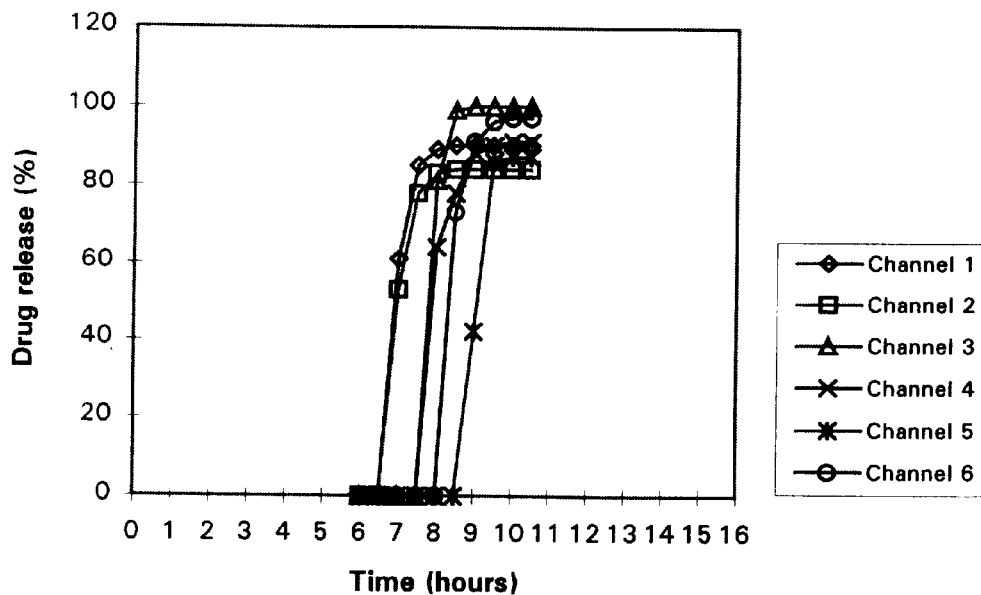
FIG. 17 is a graphic representation of an in-vitro dissolution study of six coated tablets as in Example 18.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 17):

| Diazepam | Release (%) after sampling time (in hours): | | | | | | | | | | | | |
|---|---|---|---|---|---|---|---|---|---|---|---|---|---|
| Example 18 | 5 | 5.5 | 6 | 6.5 | 7 | 7.5 | 8 | 8.5 | 9 | 9.5 | 10 | 10.5 | 11 |
| Channel 1 | 0 | 0 | 0 | 0 | 61 | 85 | 89 | 90 | 90 | 90 | 90 | 90 | 90 |
| Channel 2 | 0 | 0 | 0 | 0 | 53 | 78 | 83 | 84 | 84 | 84 | 84 | 84 | 84 |
| Channel 3 | 0 | 0 | 0 | 0 | 0 | 0 | 81 | 99 | 100 | 100 | 100 | 100 | 100 |
| Channel 4 | 0 | 0 | 0 | 0 | 0 | 0 | 64 | 78 | 88 | 90 | 91 | 91 | 91 |
| Channel 5 | 0 | 0 | 0 | 0 | 0 | 0 | 0 | 0 | 42 | 86 | 87 | 87 | 87 |
| Channel 6 | 0 | 0 | 0 | 0 | 0 | 0 | 0 | 73 | 91 | 96 | 97 | 97 | 97 |

From the experiments it can be concluded that it is possible to prepare an Oral Immediate Release formulation of diazepam, according to the present invention.

Example 19

To investigate the applicability of the present invention in the formulation of mebeverine, core tablets containing mebeverine are prepared by the procedure described in example 1, followed by coating according to the procedure described in example 1.

Composition, in mg per tablet:

| Excipients | Example 19 |
|---|---|
| Core: | |
| mebeverine | 38.6 |
| micro-crystalline cellulose | 56.0 |
| talc | 4.7 |
| cross-linked carboxymethylcellulose | 4.8 |
| Coating: | |
| ethylcellulose | 12.6 |
| Citroflex ® 2 | 2.6 |
| talc | 9.4 |
| Total | 128.7 |

Figure 18:
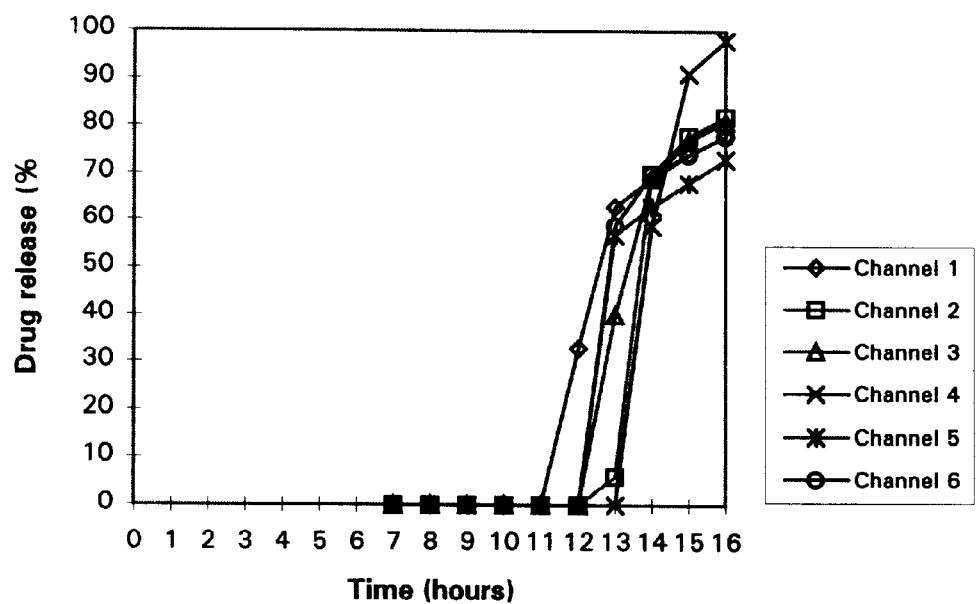
FIG. 18 is a graphic representation of an in-vitro dissolution study of six coated tablets as in Example 19.

In-vitro dissolution study of 6 coated tablets with the USP apparatus II, with half change release medium (pH=1.2 followed by pH=6.8) and a rotation speed of the paddle of 50 rpm gives the following results (also depicted in FIG. 18):

| Mebeverine | Release (%) after sampling time (in hours): | | | | | | | | | |
|---|---|---|---|---|---|---|---|---|---|---|
| Example 19 | 7.0 | 8.0 | 9.0 | 10.0 | 11.0 | 12.0 | 13.0 | 14.0 | 15.0 | 16.0 |
| Channel 1 | 0 | 0 | 0 | 0 | 0 | 33 | 63 | 69 | 74 | 78 |
| Channel 2 | 0 | 0 | 0 | 0 | 0 | 0 | 6 | 70 | 78 | 82 |
| Channel 3 | 0 | 0 | 0 | 0 | 0 | 0 | 40 | 69 | 77 | 81 |
| Channel 4 | 0 | 0 | 0 | 0 | 0 | 0 | 0 | 59 | 91 | 98 |
| Channel 5 | 0 | 0 | 0 | 0 | 0 | 0 | 57 | 63 | 68 | 73 |
| Channel 6 | 0 | 0 | 0 | 0 | 0 | 0 | 59 | 70 | 74 | 78 |

From the experiments it can be concluded that it is possible to prepare an Oral Immediate Release formulation of mebeverine, according to the present invention.

Example 20

To investigate the applicability of the present invention in the formulation of a vaccine, core tablets containing influenza vaccine are prepared by the procedure described in example 1, followed by coating according to the procedure described in example 1.

Composition, in mg per tablet:

| Excipients | Example 20 |
|---|---|
| Core: | |
| Influenza vaccine (bioactive protein) | 0.325 |
| micro-crystalline cellulose | 105.1 |
| talc | 0.6 |
| cross-linked carboxymethylcellulose | 6.7 |
| Coating: | |
| ethylcellulose | 9.6 |
| Citroflex ® 2 | 2.3 |
| talc | 7.2 |
| Total | 131.8 |

In absence of an applicable method for the measurement of the release of the bioactive protein as a function of time, the time of delay (lag time) of the release of the active compound by means of the visual appearance of the coated tablet is determined (opening of the "cover of the box"). The time of delay of 6 tablets with the USP apparatus II, with half change release medium (pH=1.2 followed by pH=6.8) and a rotation speed of the paddle of 50 rpm gives the following results:

| | Tablet 1 | Tablet 2 | Tablet 3 | Tablet 4 | Tablet 5 | Tablet 6 |
|---|---|---|---|---|---|---|
| time of delay (in minutes) | 231 | 201 | 228 | 223 | 223 | 218 |

After the release of the content of the core, the content of bioactive protein is measured. About 25% (about 75 μg per tablet) of the bioactive protein is available.

From the experiments it can be concluded that it is possible to prepare an Oral Immediate Release formulation of a bioactive protein according to the present invention.

What is claimed is:

1. An Oral Delayed Immediate Release formulation comprising a compressed substantially non-swellable core containing one or more active substances surrounded with a coating, wherein release of active substance from the core is caused by rupture of the coating upon exposure to gastrointestinal fluids after a definite delay from said exposure, said core comprising one or more immediate release carriers and said core having no substantial swelling properties upon exposure to gastrointestinal fluids.

2. An Oral Delayed Immediate Release formulation comprising a compressed substantially non-swellable core containing one or more active substances surrounded with a coating containing one or more polymeric coating materials, wherein release of active substance(s) from the core is caused by rupture of the coating upon exposure to gastrointestinal fluids after a definite delay from said exposure, said core comprising one or more immediate release carriers and said core having no substantial swelling properties upon exposure to gastrointestinal fluids, and said polymeric coating materials being essentially non-soluble and/or non-erodable in gastrointestinal fluids.

3. An Oral Delayed Immediate Release formulation according to claim 2, characterized in that said coating comprises 2–20% of a water-soluble plasticizing agent and an effective amount of a brittleness-inducing agent.

4. An Oral Delayed Immediate Release formulation according to claim 3, characterized in that said water-soluble plasticizing agent is selected from the group consisting of triethyl citrate, tributyl citrate, propylene glycol, polyethylene glycol, triacetin and sodium lauryl sulphate.

5. An Oral Delayed Immediate Release formulation according to claim 3, characterized in that said water-soluble plasticizing agent is triethylcitrate.

6. An Oral Delayed Immediate Release formulation according to claim 3, characterized in that said brittleness-inducing agent is added in an amount between 3 and 60%.

7. An Oral Delayed Immediate Release formulation according to claim 6, characterized in that said brittleness-inducing agent is selected from the group consisting of 20–40% of talc, 3–25% of aerosil and 5–60% of magnesium stearate.

8. An Oral Delayed Immediate Release formulation according to claim 7, characterized in that said brittleness-inducing agent is 20–40% of talc.

9. An Oral Delayed Immediate Release formulation according to claim 2, characterized in that said polymeric coating material essentially consists of ethylcellulose.

10. An Oral Delayed Immediate Release formulation according to claim 1, characterized in that said formulation has a diameter of more than 2 mm.

11. An Oral Delayed Immediate Release formulation according to claim 1, characterized in that said active substance is a pharmaceutical compound selected from the group consisting of anti-asthmatics, anti-emetics, cardiotonics, vasodilators, anti-vertigo and anti-meniere compounds, anti-hypertensives, sedatives, antidepressants, anti-anxiety compounds, cortico-steroids, general anti-inflammatory compounds, anti-inflammatory compounds for gastrointestinal use, anti-ulceratives, analgetics, anti-aritmics, anti-rheumatics, anti-arthritic compounds and anti-angina compounds.

12. An Oral Delayed Immediate Release formulation according to claim 1, characterized in that said active substance is a biological active compound selected from the group consisting of proteins, peptides, enzymes, vaccines and oligonucleotides.

13. An Oral Delayed Immediate Release formulation according to claim 12, characterized in that said biologically active substance is a vaccine.

14. An Oral Delayed Immediate Release formulation according to claim 13, characterized in that said vaccine is influenza vaccine.

15. An Oral Delayed Immediate Release formulation according to claim 1, characterized in that said Oral Delayed Immediate Release formulation has a certain release delay and is combined in one capsule with an Oral Immediate Release formulation and/or one or more Oral Delayed Immediate Release formulations with a different release delay.

16. An Oral Delayed Immediate Release formulation according to claim 1, characterized in that said Oral Delayed Immediate Release formulation is surrounded with an Oral Immediate Release formulation.

17. A method of preparing an Oral Delayed Immediate Release formulation comprising claim 2, (1) a core is compressed of a mixture comprising one or more active substances and one or more immediate release carriers, (2) the compressed core is coated with a mixture of coating materials, said core and said coating having the properties and/or composition as claimed in claim 1–14.

18. A method of preparing an Oral Delayed Immediate Release formulation according to claim 15–16, characterized in that (1) a core is compressed of a mixture comprising one or more active substances and one or more immediate release carriers, (2) the compressed core is coated with one or more coating materials and that (3) the first Oral Delayed Immediate Release formulation is (i) combined in a capsule with an Oral Immediate Release formulation and/or one or more Oral Delayed Immediate Release formulations with a different release delay, or (ii) surrounded with an Oral Immediate Release formulation, a mixture of coating materials, said core and said coating having the properties and/or composition as claimed in claim 15–16.

19. An Oral Delayed Immediate Release formulation according to claim 2, characterized in that said formulation has a diameter of more than 2 mm.

20. The Oral Delayed Immediate Release formulation of claim 10, wherein said formulation has a diameter of more than 5 mm.

21. The Oral Delayed Immediate Release formulation of claim 19, wherein said formulation has a diameter of more than 5 mm.

22. An Oral Delayed Immediate Release formulation according to claim 2, characterized in that said active substance is a pharmaceutical compound selected from the group consisting of anti-asthmatics, anti-emetics, cardiotonics, vasodilators, anti-vertigo and anti-meniere compounds, anti-hypertensives, sedatives, antidepressants, anti-anxiety compounds, cortico-steroids, general anti-inflammatory compounds, anti-inflammatory compounds for gastrointestinal use, anti-ulceratives, analgetics, anti-aritmics, anti-rheumatics, anti-arthritic compounds and anti-angina compounds.

23. An Oral Delayed Immediate Release formulation according to claim 2, characterized in that said active substance is a biological active compound selected from the group consisting of proteins, peptides, enzymes, vaccines and oligonucleotides.

24. An Oral Delayed Immediate Release foundation according to claim 23, characterized in that said biologically active substance is a vaccine.

25. An Oral Delayed Immediate Release formulation according to claim 24, characterized in that said vaccine is influenza vaccine.

26. An Oral Delayed Immediate Release formulation according to claim 2, characterized in that said Oral Delayed Immediate Release formulation has a certain release delay and is combined in one capsule with an Oral Immediate Release formulation and/or one or more Oral Delayed Immediate Release formulations with a different release delay.

27. An Oral Delayed Immediate Release formulation according to claim 2, characterized in that said Oral Delayed Immediate Release formulation is surrounded with an Oral Immediate Release formulation.

28. A method of preparing an Oral Delayed Immediate Release formulation according to claim 16, characterized in that (1) a core is compressed of a mixture comprising one or more active substances and one or more immediate release carriers, (2) the compressed core is coated with one or more coating materials and that (3) the first Oral Immediate Release formulation is (i) combined in a capsule with an Oral Delayed Immediate Release formulation and/or one or more Oral Delayed Immediate Release formulations with a different release delay, or (ii) surrounded with an Oral Immediate Release formulation, a mixture of coating materials, said core and said coating having the properties and/or composition as claimed in claim 16.

* * * * *